United States Patent [19]

Drent et al.

[11] 4,249,031
[45] Feb. 3, 1981

[54] PROCESS FOR THE PREPARATION OF A HYDROCARBON MIXTURE

[75] Inventors: Eit Drent; Ringnerus P. van der Werf, both of Amsterdam, Netherlands

[73] Assignee: Shell Oil Company, Houston, Tex.

[21] Appl. No.: 133,704

[22] Filed: Mar. 25, 1980

[30] Foreign Application Priority Data

Apr. 12, 1979 [NL] Netherlands ......................... 7902886

[51] Int. Cl.³ .............................................. C07C 1/20
[52] U.S. Cl. ................................................... 585/733
[58] Field of Search ........................................ 585/733

[56] References Cited

U.S. PATENT DOCUMENTS

| | | | |
|---|---|---|---|
| 2,492,984 | 1/1950 | Grosse et al. | 585/733 |
| 3,969,427 | 7/1976 | Bell et al. | 585/733 |
| 4,059,646 | 11/1977 | Wald et al. | 585/733 |
| 4,059,647 | 11/1977 | Wald et al. | 585/733 |
| 4,126,642 | 11/1978 | Kim et al. | 585/733 |
| 4,166,189 | 8/1979 | Wald et al. | 585/733 |

*Primary Examiner*—Curtis R. Davis
*Attorney, Agent, or Firm*—Ronald R. Reper

[57] ABSTRACT

Method for the production of hydrocarbon comprises contacting as feed low molecular weight oxygenated organic compounds with a zinc halide in the presence of certain high-boiling, low vapor pressure compounds having good solvency for the zinc halide.

10 Claims, No Drawings

PROCESS FOR THE PREPARATION OF A HYDROCARBON MIXTURE

BACKGROUND OF THE INVENTION

The invention relates to a process for the preparation of a hydrocarbon mixture, in which one or more oxygen-containing organic compounds are contacted with one or more zinc halides at elevated temperature.

Processes for the conversion of organic oxygenates to hydrocarbons using molten zinc halides are known, and described, for example, in U.S. Pat. No. 2,492,984 and U.S. Pat. No. 3,969,427.

A similar process to that according to the present invention is known from U.S. Pat. Nos. 4,059,646 and 4,059,647. Both patent specifications describe a process for the preparation of triptane, in which methanol, dimethyl ether or mixtures thereof are contacted with zinc bromide and zinc iodide, respectively, at a temperature of 210°–245° C. and 180°–240° C., respectively.

According to the examples in said patent specifications, relatively large quantities of zinc halide are used in relation to the quantity of methanol to be converted.

It has now been found that the quantity of zinc halide required for the process can be drastically reduced, while the reaction time is found to be short and a valuable hydrocarbon mixture is obtained, if the process is carried out in the presence of a high boiling compound which has a melting point which is lower than the temperature at which the process is carried out and a vapor pressure at said temperature which is at most 0.05 of the pressure of the oxygen-containing organic compound(s), and in which the oxygen-containing organic compound(s) and zinc halide are soluble.

SUMMARY OF THE INVENTION

The invention therefore relates to a process for the preparation of a hydrocarbon mixture, in which one or more oxygen-containing organic compounds are contacted with one or more zinc halides at elevated temperature, characterized in that the process is carried out in the presence of a high-boiling compound which has a melting point which is lower than the temperature at which the process is carried out and a vapor pressure at said temperature which is at most 0.05 of the pressure of the oxygen-containing organic compound(s), and in which the oxygen-containing organic compound(s) and zinc halide are soluble.

DESCRIPTION OF THE PREFERRED EMBODIMENTS

Oxygen-containing organic compounds which can be used in the process according to the invention are preferably lower aliphatic compounds, e.g., aliphatic alcohols (particularly methanol), ethers (particularly dimethyl ether), ketones (particularly acetone), carboxylic esters and/or aldehydes, for example acetaldehyde, carboxylic acids, for example acetic acid, polyhydric alcohols and carboxylic anhydrides. The oxygen-containing compounds may have up to about 8 preferably up to about 4 carbon atoms in one or more portions attached to the oxygen atom.

The starting materials containing the above-mentioned oxygen-containing compounds may of course be obtained from any usual source. Methanol derived from synthesis gas obtained from coal and methanol prepared from natural gas, for example, are extremely suitable.

At the temperature at which the process is carried out the high-boiling compound preferably has a vapor pressure in the range from $10^{-3}$ to 0.5 bar. In the case of a vapor pressure below $10^{-3}$ bar there is a great chance that the compound is in the solid phase under the reaction conditions. A vapor pressure in excess of 0.5 bar implies that the compound evaporates excessively under the reaction conditions. The high-boiling compounds which are suitable include the alcohols having 10 to 23 carbon atoms, such as dodecanol, heptadecanol, nonadecanol and pentadecanol, and further the ethers having 14–24 carbon atoms, such as didodecyl ether, tetradecyl tetracosanyl ether, dinonyl ether and dipentadecyl ether. Other high-boiling solvents having a boiling point above 210° C., which are liquid under the reaction conditions of the process are suitably employed according to the invention.

Of the alcohols heptadecanol is most preferred. Of the ethers most preference is given to didodecyl ether. The conversion of oxygen-containing organic compound(s) into hydrocarbons is found to be highest in the use of heptadecanol or didodecyl ether.

Good results are obtained if the quantity of high-boiling compound in relation to the quantity of zinc halide is 5–25% by weight.

Exemplary zinc halides include zinc chloride, zinc bromide and zinc iodide.

Zinc iodide is preferably used on account of its great activity as zinc halide. It has been established experimentally that a. a high-boiling compound must be used to which applies that the solubility therein of zinc halide at 100° C. is preferably at least 1 mol/liter. The process will prove to be economically unattractive if the solubility is less than 1 mol/l.

b. The pressure at which the process is carried out is preferably in the range from 1 to 80 bar, at which pressure the organic oxygen compound to be converted must be present in the vapor phase. Operation of the process at pressures higher than 80 bar and below 1 bar is economically disadvantageous.

c. The temperature at which the process is carried out is preferably in the range from 170° to 250° C. At temperatures below 170° C. the conversion reaction proceeds too slowly.

Temperatures above 250° C. may adversely affect the conversion process because undesired side-reactions such as cracking and carbonization reactions may take place, with the result that the yield of the desired hydrocarbon mixture is affected unfavorably.

The process according to the invention can also advantageously be carried out with zinc halide on a carrier, for example silica or alumina or combinations thereof. The process according to the invention can be carried out batchwise or continuously.

Irrespective of the chosen process, a good degree of mixing or contact between the zinc halide and the organic oxygen compound(s) is important to obtain good results. It is possible to use any reaction system in which a high degree of mixing or contact between said compound(s) and zinc halide is obtained. Use can be made, for example, of systems having fixed beds or slurry reactors. The contact times are not of special importance and experts may vary these times to obtain optimum results which are also dependent on, for example, the volumes of the reactants, reactor type, temperature, etc. When use is made, for example, of a reactor with fixed bed and continuous flow of the reactants, contact times of about 0.5 to 180 minutes and even longer periods can be used. In batchwise operation the contact times may be considerably longer.

The invention will be further illustrated with reference to the following examples to which the invention is not limited, however.

EXAMPLE I

Quantities of 10.4 g of zinc iodide, 2.1 g (2.6 ml) of methanol and 0.2 g (0.25 ml) of heptadecanol were charged to a 200 ml autoclave, whereupon the autoclave was sealed airtight. The mixture was stirred and heated at 205° C. for 1 hour. The pressure rose to 13 bar. The reactor was subsequently cooled to room temperature. Gaseous product was discharged into a gasometer. Liquid product was distilled over at 160° C. from the reactor to a cooled collecting vessel, initially at atmospheric pressure, while nitrogen was blown through in order to promote the distillation (30 minutes), subsequently at reduced pressure (30 minutes at 20 mm Hg, then 15 minutes at 2 mm (Hg). The heptadecanol remained behind on the zinc iodide.

The liquid product in the cooled collecting vessel consisted of two layers, an aqueous layer and a layer of hydrocarbon oil. The bottom layer consisted mainly of water and less than 0.88 g of methanol was present. The layer of hydrocarbon oil, which had a weight of 0.53 g, had the following analysis:

|  | % by weight |
|---|---|
| 2-methyl propane | 0.72 |
| n-butane | 1.23 |
| 2,2-dimethyl propane | 0.64 |
| n-pentane | 1.90 |
| 2,2-dimentyl butane | 0.02 |
| 2,3-dimethyl butane | 1.35 |
| 2-methyl pentane | 0.36 |
| 3-methyl pentane | 0.28 |
| n-hexane | 0.14 |
| 2,2,3-trimethyl butene-1 | 5.72 |
| 2,4-dimethyl pentane | 0.37 |
| 2,2,3-trimethyl butane | 17.8 |
| 2,3-dimethyl pentane | 0.72 |
| 2-methyl hexane | 0.18 |
| 3-methyl hexane | 0.21 |
| n-heptane | 0.64 |
| butenes | 0.42 |
| pentenes | 2.27 |
| hexenes | 0.52 |
| heptenes | 1.12 |
| octenes | 1.40 |
| 2,2,4-trimethyl pentane | 0.31 |
| 2,2,3,3,-tetramethyl butane | 0.46 |
| 2,5-dimethyl hexane | 0.31 |
| 2,2-dimethyl hexane | 0.33 |
| 2,2,3-trimethyl pentane | 11.83 |
| 3,3-dimethyl hexane | 0.81 |
| 2,3,4-trimethyl pentane | 0.69 |
| 2,3,3-trimethyl pentane | 1.41 |
| 3,4-dimethyl hexane | 0.25 |
| n-octane | 0.16 |
| higher boiling than n-octane | 43.65 |
| Total | 100 |

EXAMPLE II

In this experiment use was made of a catalyst consisting of ZnI$_2$/heptadecanol on a carrier of silica spheres having an average diameter of 15 nm and pores with an average diameter of 2.5 nm. This catalyst was prepared as follows:

100 g of ZnI$_2$ was dissolved in 60 ml of methanol, to which 5 g of heptadecanol was subsequently added. To this solution 100 g of silica in the above-mentioned form was added so that the silica was impregnated with the solution. The catalyst material was subsequently dried at 120° C.

For the experiment 20.3 g of said catalyst and 2.1 g (2.6 ml) of methanol were charged to a 200 ml autoclave, whereupon the autoclave was sealed airtight. The mixture was stirred and heated at 205° C. for 1 hour. The pressure rose to 15 bar. The reactor was subsequently cooled to room temperature.

Gaseous product was discharged into a gasometer. Liquid product was distilled over at 160° C. from the reactor to a cooled collecting vessel, initially at atmospheric pressure, while nitrogen was blown through as in Example I (30 minutes), subsequently at reduced pressure (30 minutes at 20 mm HG, subsequently 15 minutes at 2 mm Hg). The heptadecanol remained behind on the zinc iodide.

The liquid product in the cooled collecting vessel consisted of two layers, an aqueous layer and a layer of hydrocarbon oil. The bottom layer consisted mainly of water and less than 0.3 g of methanol was present. The layer of hydrocarbon oil, which had a weight of 0.8 g, had the following analysis:

|  | % by weight |
|---|---|
| 2-methyl propane | 1.18 |
| n-butane | 0.87 |
| 2,2-dimethyl propane | 0.82 |
| 2-methyl butane | 1.06 |
| n-pentane | 2.16 |
| 2,2-dimethyl butane | 0.03 |
| 2,3-dimethyl butane | 0.64 |
| 2-methyl pentane | 0.21 |
| 3-methyl pentane | 0.16 |
| n-hexane | 0.16 |
| 2,2,3-trimethyl butene-1 | 4.56 |
| 2,4-dimethyl propane | — |
| 2,2,3-trimethyl butane | 8.07 |
| 2,3-dimethyl pentane | 0.32 |
| 2-methyl hexane | 0.20 |
| 3-methyl hexane | 0.15 |
| n-heptane | 0.52 |
| butenes | 0.52 |
| pentenes | 2.16 |
| hexenes | 0.41 |
| heptenes | 1.03 |
| octenes | 0.95 |
| 2,2,4-trimethyl pentane | 0.14 |
| 2,2,3,3-tetramethyl butane | 0.38 |
| 2,5-dimethyl hexane | 0.13 |
| 2,2-dimethyl hexane | 0.26 |
| 2,2,3-trimethyl pentane | 23.1 |
| 3,3-dimethyl hexane | 0.37 |
| 2,3,4-trimethyl pentane | 0.34 |
| 2,3,3-trimethyl pentane | 0.99 |
| 3,4-dimethyl hexane | 0.11 |
| n-octane | — |
| higher boiling than n-octane | 48.1 |
| Total | 100 |

EXAMPLE III

Quantities of 10.4 g of zinc iodide and 0.2 g (0.25 ml) of heptadecanol were charged to a 200-ml autoclave and subsequently 1.51 g of dimethyl ether was supplied to the autoclave at a pressure of 5 bar at room temperature.

The mixture was stirred and heated at 205° C. for 1.5 hours. The pressure rose to 12 bar. The reaction product was worked up in the same manner as in Example I.

A layer of hydrocarbon oil having a weight of 0.92 g was formed, which layer was not analyzed further.

EXAMPLE IV

Quantities of 10.4 g of zinc iodide, 2.1 g (2.6 ml) of acetone and 0.2 g (0.25 ml) of heptadecanol were charged to an autoclave under nitrogen, whereupon the autoclave was sealed airtight.

The pressure rose to 9 bar and the mixture was stirred and heated at about 180° C. for 1 hour. The reactor was subsequently cooled to room temperature. Gaseous product was discharged into a gasometer. Liquid product was distilled over at 160° C. from the reactor to a cooled collecting vessel, initially a atmospheric pressure, while nitrogen was blown through as in Example I (30 minutes), and subsequently at reduced pressure (30 minutes at 20 mm Hg and subsequently 15 minutes at 2 mm Hg). The material remaining in the autoclave was removed by washing with water.

The quantity of gaseous product was small and consisted mainly of isoparaffins. The liquid product present in the cooled collecting vessel consisted of two layers, an aqueous layer and a layer of hydrocarbon oil. The layer of hydrocarbon oil, which was not analyzed, had a weight of 0.8 g.

EXAMPLE V

In order to demonstrate the effect of the high-boiling compound on the degree of conversion of the oxygen-containing compound(s) a comparative experiment was carried out which differs from the experiment of Example I only in the fact that no high-boiling compound was used.

After the product had been processed, it was found that no detectable quantity of hydrocarbon oil had formed.

What is claimed is:

1. A process for the preparation of a hydrocarbon mixture, comprising contacting one or more oxygen-containing organic compounds in the vapor phase with one or more zinc halides in a contact zone at elevated temperature in the presence of a high-boiling compound which has a melting point which is lower than the temperature at which the process is carried out, and a vapor pressure at said temperature which is at most 0.05 of the pressure of the oxygen-containing organic compound(s), and in which the oxygen-containing organic compound(s) and zinc halide are soluble.

2. A process as in claim 1, wherein the high-boiling compound has a vapor pressure in the range from $10^{-3}$ to 0.5 bar at a temperature at which the process is carried out.

3. A process as in claim 1, wherein said high-boiling compound has a solubility in said zinc halide at 100° C. of at least 1 mol/l.

4. A process as in claim 1, wherein said high-boiling compound is selected from the group consisting of alcohols having 10–23 carbon atoms, ethers having 14–24 carbon atoms, and mixtures thereof.

5. A process as in claim 4 wherein said high-boiling compound is selected from heptadecanol and didodecyl ether.

6. A process as in claim 1, wherein the quantity of high-boiling compound in said contact zone is 5–25% by weight of the quantity of zinc halide.

7. A process as in claim 1, wherein the zinc halide is zinc iodide.

8. A process as in claim 1, wherein said zinc halide is supported on a carrier containing at least one of silica and alumina.

9. A process as in claim 1, wherein the pressure in said contacting zone is in the range from 1 to 80 bar.

10. A process as in claim 1, wherein the temperature in said contacting zone is in the range from 170°–250° C.

* * * * *